(12) United States Patent
Helmer et al.

(10) Patent No.: US 8,291,779 B2
(45) Date of Patent: Oct. 23, 2012

(54) SYSTEM AND GARMENT FOR DETECTING MOVEMENT

(75) Inventors: Richard James Neil Helmer, Geelong (AU); Michael Anthony Mestrovic, Moriac (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 846 days.

(21) Appl. No.: 12/089,786

(22) PCT Filed: Oct. 13, 2006

(86) PCT No.: PCT/AU2006/001521
§ 371 (c)(1),
(2), (4) Date: Sep. 2, 2008

(87) PCT Pub. No.: WO2007/041806
PCT Pub. Date: Apr. 19, 2007

(65) Prior Publication Data
US 2009/0095094 A1     Apr. 16, 2009

(30) Foreign Application Priority Data
Oct. 13, 2005  (AU) .............................. 2005905666

(51) Int. Cl.
*G01L 5/16*  (2006.01)

(52) U.S. Cl. ..................................................... 73/865.4

(58) Field of Classification Search ................. 73/865.4
See application file for complete search history.

(56) References Cited

U.S. PATENT DOCUMENTS

| | | | |
|---|---|---|---|
| 3,908,279 A | 9/1975 | Yoslow et al. | |
| 4,108,164 A * | 8/1978 | Hall, Sr. .................... | 600/594 |

(Continued)

FOREIGN PATENT DOCUMENTS

WO         8907236 A1     8/1989

(Continued)

OTHER PUBLICATIONS

European Search Report corresponding to EP 06 79 0386 dated Dec. 1, 2009.

(Continued)

*Primary Examiner* — Hezron E Williams
*Assistant Examiner* — Rodney T Frank
(74) *Attorney, Agent, or Firm* — Sughrue Mion, PLLC

(57) ABSTRACT

According to the present invention there is provided a system for detecting movement, for example and without limitation, for detecting movement of a part of a person such as their limb or a section of their limb or deformable surface. The system preferably includes: a) an electrical power source; two or more than two contactors that can be mounted directly or indirectly to parts of a person or object that move relative to each other; and c) an electrical element that, when in use, conducts an electrical current and is in electrical connection with the contactors, wherein the element is substantially unextendable along its longitudinal axis and the element is either i) at least in part resiliently deformable in a direction transverse to its longitudinal axis and/or ii) supported directly or indirectly by a guide structure having elastic properties that is configured to minimize deformation of the element in a direction transverse to its longitudinal axis such that the effective length of the element that defines a path of least electrical resistance between the contactors is minimized, and wherein relative movement of the contactors can cause the effective length of the element between the contactors to change such that movement can be measured or detected as a change in electrical resistance between the contactors.

16 Claims, 4 Drawing Sheets

U.S. PATENT DOCUMENTS

| | | | |
|---|---|---|---|
| 4,715,235 A * | 12/1987 | Fukui et al. | 73/862.68 |
| 5,047,952 A | 9/1991 | Kramer et al. | |
| 5,052,375 A * | 10/1991 | Stark et al. | 601/34 |
| 5,086,785 A | 2/1992 | Gentile et al. | |
| 5,166,463 A * | 11/1992 | Weber | 84/600 |
| 5,368,546 A * | 11/1994 | Stark et al. | 601/34 |
| 5,484,389 A * | 1/1996 | Stark et al. | 601/34 |
| 5,570,301 A * | 10/1996 | Barrus | 702/150 |
| 5,862,803 A * | 1/1999 | Besson et al. | 600/508 |
| 6,032,530 A | 3/2000 | Hock | |
| 6,119,516 A * | 9/2000 | Hock | 73/379.01 |
| 6,148,280 A * | 11/2000 | Kramer | 702/153 |
| 6,428,490 B1 * | 8/2002 | Kramer et al. | 600/595 |
| 6,487,906 B1 | 12/2002 | Hock | |
| 7,070,571 B2 * | 7/2006 | Kramer et al. | 600/595 |
| 7,215,991 B2 * | 5/2007 | Besson et al. | 600/509 |
| 2003/0083596 A1 | 5/2003 | Kramer et al. | |
| 2005/0054941 A1 | 3/2005 | Ting | |

FOREIGN PATENT DOCUMENTS

| | | |
|---|---|---|
| WO | 03/014684 A1 | 2/2003 |
| WO | 03/060449 A1 | 7/2003 |

OTHER PUBLICATIONS

Bickerton et al., "Effects of Fiber Interactions on Conductivity within a Knitted Fabric Stretch Sensor", IEE, Jan. 1, 2003, pp. 67-72, G.B. Gibbs, et al, "Wearable Conductive Fiber Sensors for Multi-Axis Human Joint Angle Measurement", Journal of Neuro Engineering and Rehabilitaion, Mar. 2, 2005.

European Examination Report in corresponding European Patent Application No. 06790386.4 dated Jun. 11, 2012.

* cited by examiner

SYSTEM AND GARMENT FOR DETECTING MOVEMENT

FIELD AND BACKGROUND OF THE PRESENT INVENTION

The present invention relates to a system and garment for detecting or monitoring the movement of a person, animal or an object such as a machine and in particular the movement of parts thereof. For example, the present invention can be used for monitoring or detecting the movement of the arms and legs of an athlete or patient. Similarly, the present invention may also be used for monitoring or detecting the movement of a robot or machine.

The technology that is the subject of the present invention may find use in a broad range of applications including, but by no means exhaustively, training or rehabilitating skeletal joints or muscular injuries, biomedical monitoring, medical textiles, triage service for injured soldiers and other military and security applications. According to another example, the present invention may be used as a tool in adjusting the shape or configuration of a medium such as textiles, and more specifically the shape and configuration of a sail of the yacht. According to yet another example, the present invention may be applied to musical instruments where the sound produced is a function, or controlled, by the movement of a person or object.

An example of a system that measures the movement of a human hand is described in U.S. Pat. No. 6,701,296. The system comprises a series of goniometers that detect hinge like movements or joint movement in a person's hand. Joint movement is monitored using a series of strain gauges that change in electrical conductivity as the strain gauges are stressed. Each strain gauge forms part of a glove worn by a person and the strain gauges are located on the palm or upper faces of the glove. Changes in electrical signal are received when the person curls their fingers and the electrical signals may then be interpreted to carry out specific functions using computer interfaces.

Another example is that the device described in a paper entitled "A WEARABLE CONDUCTIVE FIBER SENSORS FOR MULTI-AXIS HUMAN JOINT ANGLE MEASUREMENTS", by Peter Gibbs and Harry Asada, Journal of NeuroEngineering and Rehabilitation 2005, 2:7. The paper describes a device in the form of a conventional knee support comprising a knitted fabric sleeve containing rayon, cotton, and rubber. An electrical conductive fibre is permanently attached to the knee support above the knee joint at one conductive point, and spans across the joint on the outside of the knee support fabric. The conductive fibre is not sewn or woven into the sleeve, as it needs to freely slide across the joint. Coupled to the opposite end of the conductive fibre is an elastic cord which is permanently attached to the sleeve at a position that is below the knee when worn and places the conductive fibre under tension during use. As the joint moves, the elastic cord changes length, pulling the conductive fibre past another conductive point that is permanently stitched into the fabric so as to form a circuit between the conductive points. As the joint is flexed, the length of the conductive fibre between the conductive point increases and electrical resistance between the two conductive points is measured using a voltage divider or bridge circuit. Ultimately, changes in resistance can be interpreted and analysed to provide information relating to joint movement.

In order to maintain reliable operation, the device is dependant on the elastic cord maintaining the conductive fibre under tension at all times. In the event of the elastic cord failing, the length of the conductive fibre between the points will not be representative of the degree of flex in the knee joint. In addition, in our view the design is not particularly suited to situations where the conductive fibre is located in the inside of the joint such as behind a knee or on the inside of an elbow.

It is an object of the present invention to provide an alternative system that can be used for monitoring the movement of a joint or deformed surface.

SUMMARY OF INVENTION

According to the present invention there is provided a system for detecting movement, for example and without limitation, for detecting movement of a part of a person such as their limb or a section of their limb or deformable surface. The system including:
  a) two or more than two contactors that can be mounted directly or indirectly to parts of a person or object that move relative to each other, such that when in use, the spacing between the connectors can change as a result of the person or object moving; and
  b) an elongate electrical element that, when in use, conducts an electrical current and is in electrical connection with the contactors, wherein the element is substantially un-extendable along its longitudinal axis and the element is either i) at least in part resiliently deformable in a direction transverse to its longitudinal axis and/or ii) supported directly or indirectly by a guide structure having elastic properties that is configured to minimise deformation of the element in a direction transverse to its longitudinal axis such that the effective length of the element that defines a path of least electrical resistance between the contactors is minimised, and wherein relative movement of the contactors can cause the effective length of the element between the contactors to change such that movement can be measured or detected as a change in electrical resistance between the contactors.

An advantage provided by the present invention is that movement of the object can be easily detected and analysed by monitoring changes in electrical resistance between the contactors. Another advantage provided by the present invention is that on account of the resilient nature of the element, the system has a relative straightforward and simple structure.

It is preferred that the resilient deformable nature of the element and/or the elastic properties of the guide structure minimises the degree of curvature in the element between the contactors. The electrical resistance of the element is a function of its length and, therefore, by minimising the curvature of the element between the contactors the effective length of the element and the path of the least resistance is also minimised.

Although it is possible that the contactors may be individual components that can be directly fixed to the object or person whose movement is being detected or monitored by way of straps, adhesives or any other suitable means, it is preferred that the system include a flexible substrate on which the contactors are mounted and that the substrate be able to be fitted to the parts being monitored. More particularly, the substrate can be fitted to the object so that the contactors are aligned with the parts being monitored.

It is even more preferred that the substrate be capable of taking up the shape of the object such that the contactors are held in substantially the same position on the object during movement.

It is still even further preferred that the substrate be a textile and may include an elastic material such as but by no means limited to: nylon, rubber, spandex, and Lycra™.

It is preferred that the system further include a power source in electrical connection with the element.

It is also preferred that the system include means for recording the variations in electrical resistance between the contactors.

It is even preferred that said means for recording the variations in electrical resistance include a computer for analysing the electrical resistance and analysing movement of the object.

Three alternative embodiments of the present invention, each relating to how the effective length of the element is minimised and thus define a path of least resistance, will now be described in detail.

According to a first embodiment it is preferred that the element be slidably connected to at least one of the contactors such that when the contactors are moved apart the element slides through said contactor under tension and when the contactors are moved toward each other the resilient deformable nature of the element enables the element to slide through the contactor. The resilient deformable nature of the element enables the element to slide through the contractor without the element buckling and in particular, while minimizing the curvature of the element.

According to this embodiment it is also possible that the element may be slidably connected to both contactors and that the element be placed under tension when the contactors move apart, and placed under compression when the contactors move toward each other. Irrespective of whether the element is slidably connected to one or more contactors, the resilient deformable nature of the element ensures that any curvature is as smooth as possible between the contactors. As a result, the effective length and thus the path of least electrical resistance between the contactors is minimized.

In addition, it is envisaged that when the contactors move toward or away from each other, the movement of the contactors occur over a plane. In this regard, although it is possible that the element may be arranged transversely to the plane over which the contactors move, it is preferred that the element be arranged substantially parallel or co-planar to the plane over which the contactors move. In this situation, it may be said that the element is arranged in essentially an I-shaped or linear configuration between the contactors.

It is also possible for the element to have a curved tail portion that is not located between the contractors. In this situation, it may be said that the element is essentially held in a J-shape configuration.

According to a second embodiment, it is preferred that the element be fixedly connected to at least two contactors and that the electrical element be configured such that the element between the contactors includes a non-linear section of element and that a short circuit means electrically isolates the non-linear section from the effective length of the element that defines a path of least electrical resistance, and during use, the length of the element contained in the non-linear section changes as the distance between the contactors changes and in-turn changes the effective length of the element defining the path of least resistance.

It is preferred that the non-linear section be a section that changes in direction by at least 180 degrees.

It is preferred that the short circuit means be a point where the element contacts itself, and that the non-linear section include at least a 360 degree loop in the element that can vary in size such that the effective length of the element between the contactors also changes as the size of the loop changes. In this situation, it may be said that the non-linear section of the element and adjacent sections of the element has an e-shape and may include more than a 360 change in direction of the element.

For example, when the contactors are moved toward each other, the resilient nature of the element causes the size of the loop to increase and thereby reduce the length of the element between the contactors defining the path of least electrical resistance. Conversely, when the contactors are moved apart, the size of the loop decreases and thereby increases the length of the element between the contactors defining the path of the least electrical resistance.

It is preferred that the short circuit means include a bridge portion that connects to and spans across the non-linear section of the element.

It is even more preferred that the non-linear section of the element includes at least one U-shape in the element and that the bridge exclude from the effective length of the element the non-linear section of the element. In the situation where the element includes two U-shapes and two bridge portions, the element will in effect have non-linear sections and it may be said that the element has an S-shape.

According to a third embodiment, it is preferred that said element includes two or more than two sub-elements and that each sub-element be in contact with at least one other sub-element to from one or more than one sub-elements, and relative movement of the point of interconnection causes the point of interconnection to shift and in turn cause the effective length of the element defining the path of least resistance to change.

The sub-elements may be arranged such that the axis of the element is substantially parallel or transverse to one another. In the situation where the sub-elements are arranged parallel to one another, it is preferred that the sub-elements be slidably interconnected in a manner that enables one sub-element to slidably interconnect along at least one other element.

It is even more preferred that the sub-elements be interconnected at two points of interconnection and that the elements are connected as through they are connected in parallel relationship.

It is even more preferred that each sub-element include an end hook that engages the adjacent sub-element and thereby defines the point of interconnection.

In the situation where the sub-elements are arranged transversely to one another, the sub-elements contact at a point of interconnection and that the path of least electrical resistance between the sub-elements is defined along the portion of the sub-element in connect with the sub-elements and the point of interconnection.

The point of interconnection is able to move along at least one of the sub-elements in response to relative movement between the contactors.

In the situation where the sub-elements are arranged transversely to one another in an X-shape manner and adjacent ends of the sub-elements are in fixed connection with the contactors and the point of interconnection is at the centre of the X-shape, the effective length of the sub-elements essentially forms a V-shape.

According to the present invention there is provided a garment for detecting movement of a part of a person such as their limb or a section of their limb, the garment including:
 a) two or more than two contactors directly or indirectly mounted to selected positions on the garment, such that when the garment is worn the spacing between the connectors can change as a result of the person moving; and
 b) an elongate electrical element that, when in use, conducts an electrical current and is in electrical connection with the contactors, wherein the element is substantially un-extendable along its longitudinal axis and the element is either i) at least in part resiliently deformable in a direction transverse to its longitudinal axis and/or ii) supported directly or indirectly by a guide structure having elastic properties that is configured to minimise deformation of the element in a direction transverse to its longitudinal axis such that the effective length of the element that defines a path of least electrical resistance between the contactors is minimised, and wherein relative movement of the contactors can cause the effective length of the element between the contactors to change such that movement can be measured or detected as a change in electrical resistance between the contactors.

The garment of the present invention may also include any one or a combination of the features of the system of the invention.

The garment may be used for detecting or monitoring the movement of any bodily joint such the elbow, wrist, finger, shoulder, neck, back, hip, knee, ankle or toe. In the situation where the garment is a shirt or top worn by a person, the present invention may be used to monitor the relative angular positions of the elbows of the person to control an output, such as the sound of a guitar. For a more detailed explanation on how the relative angular positions of a person's elbow can be used to control and simulate the sound of a musical instrument such as a guitar, please refer our pending Australian provisional patent application no. 2006903501 and subsequent applications lodged in respect thereof. The full contexts of the specification of the provisional application and any later filed application based thereon are hereby incorporated into this specification by express cross reference.

BRIEF DESCRIPTION OF THE DRAWINGS

Preferred embodiments of the present invention will now be described with reference to the accompanying figures, of which.

DETAILED DESCRIPTION

Figure 1:
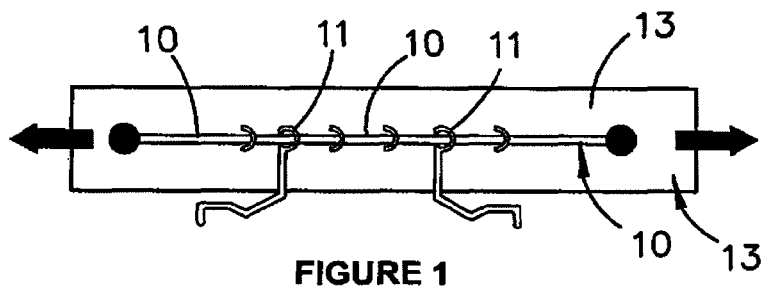
FIGS. 1 and 2 are schematic illustrations of a motion detector suitable for mounting on a textile substrate according to a first embodiment of the present invention.

The embodiments include a number of features that are the same or substantially similar and, therefore, as a matter of convenience the same reference numerals have been used throughout the detailed description and in the Figures to identify these features.

Each figure illustrates a motion detector or motion detecting system including an elongate electrical element 10 that is resiliently deformable in a direction transverse to its longitudinal axis. In other words, the electrical element 10 has an ability to recoil when deformed or bent in a direction transverse to its axis. In addition, the electrical element 10 is substantially non-extendable in a direction parallel to its axis and as a result, the element can not be temporarily or permanently stretched to substantially alter the length of the element.

Another feature common to each embodiment is a power source that includes two or possibly even more than two contactors in electrical connection with the element. Each contactor may be one of either: i) a fixed connection point 11 where the power source is fixedly connected to the element; or ii) a floating connection point 12 where the point of connection between the element 10 and the power source is able to slide along the element 10 and, thereby, provide a means by which to change the effective length of the element 10 defining the path of least electrical resistance between the power source connection points.

The floating connection points 12 are provided by a conductive thread, e.g. a silver coated nylon conductive yarn (such as Shieldex silver plated nylon yarn 125/17 2 ply) being sewn, woven, or knitted in the textile substrate that form loops or openings and the element 10 is threaded through one or more loops. Ideally, the loops are twisted from its normal unstressed position. Twisting the loops in this manner encourages a continuous electrical connection between the element 10 and the connection points 11.

The power source supplies an electrical potential difference to the connection points 11, 12 which results in the element 10 conducting an electrical current. The magnitude of the current conducted along the element 10 is determined by the resistance between the connection points 11, 12 and the resistance of the element 10 is a function of the effective length of the element 10 which equates to the length of the element 10 along which the current is conducted. Although not shown in the Figures, current conducted along the element 10 can be analysed using suitable computer hardware and software to measure, monitor, record, and assess the movement of the person or machine. The computer software may employ any suitable algorithms and can be calibrated using known techniques depending on the particular application of the system.

In use, the connection points 11, 12 are mounted to a person or machine whose movement is being monitored and more particularly, the relative movement of the connection points 11, 12 is able to be monitored by virtue of changes in the effective length of the element 10 which determines the electrical current conducted between the connection points.

The embodiments shown in the figures illustrate three different mechanisms that enable the effective length of the element 10 defining the path of least resistance to change in response to movement such as a knee or elbow flexing. The embodiment will now be described in detail.

FIG. 1 illustrates a first embodiment which includes two connection points 11 that are adapted so that the element can slide through each. The connection points 11 can be either directly or indirectly mounted to the person or machine being monitored. In the case of the embodiment shown in FIG. 1, the connection points are incorporated in a stretchable textile 13 at a fixed location in the textile and in use, the textile substrate 13 is aligned so as to fit over a joint of a person such as a knee or elbow or of a joint of a machine such as coupling or ball joint.

As the joint is moved between flexed and retracted or relaxed positions, the textile 13 stretches and retracts in response and, therefore, the distance between the connection points 11 changes with the joint flexing. As the connection points 11 move apart, the element 10 slides through said connection points 11 under tension and when the connection points 11 are moved toward each other, the resilient nature of the element 10 enables the element 10 to slide through the connection points 11 under compression. The element 10 is located on the outside of the textile and anchor to the textile at one end.

The resilient deformable nature of the element 10 ensures that the element 10 is held essentially linearly between the connection points 11 which minimises the length of the element 10 and, thus, the electrical resistance between the connection points 10.

Figure 2:
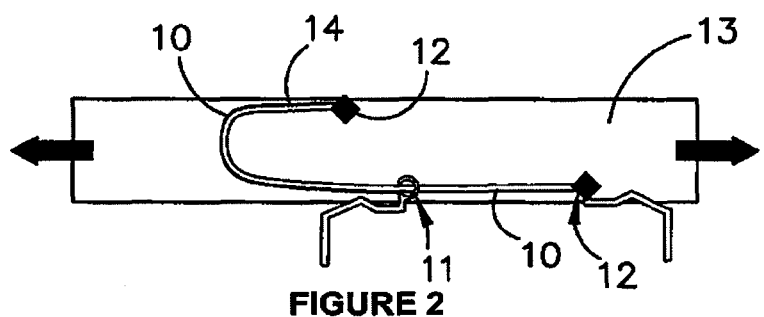

The embodiment shown in FIG. 2 is substantially the same as the embodiment shown in FIG. 1, save for the inclusion of a J or U-shaped tail portion 14 the end of which is anchored to the textile 13. The end of the element opposite to the J or U shaped tail portion includes a connection point 12 that is fixedly connected to the element and anchored to the textile substrate 13. A floating connection point 11 incorporated or mounted to the textile substrate 13 is then slidably connected to the element 10. In use, movement of a joint stretches the textile substrate 13 which in turn increases or decreases the distance between the connection points 11 and 12. In response to the distance between the connection points changing, the curvature of the tail portion 14 of the element will also change.

Figure 3:
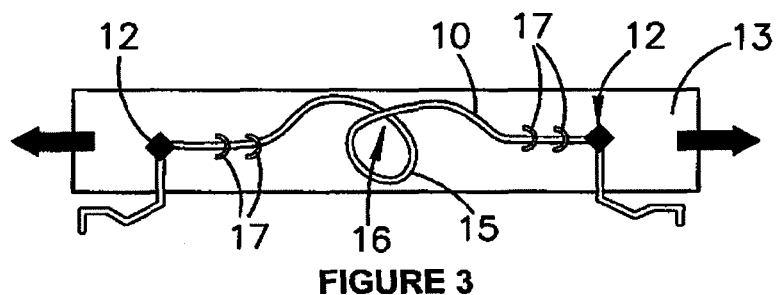
FIGS. 3 and 4 are schematic illustrations of an alternative motion detector suitable for mounting to a textile substrate according to a second embodiment of the present invention.

FIG. 3 illustrates an alternative embodiment where the connection points 12 are fixedly connected to opposite ends of the element 10 and the connection points 12 are anchored to the substrate 13. As can be seen in the FIG. 3 the element 10 overlaps and contacts itself at point 16 so as to form an e-shaped loop 15. At point 16 a short circuit is formed such that the length of the element 10 contained in the loop 15 does not contribute to the effective length of the element 10 since electrical current conducted along the element 10 bypasses the loop 15. In use, movement of the joint to which the embodiment is fitted causes the connection points 12 to move away or toward each other which in turn causes the size of the loop 15 to change and, therefore, the total length of the element 10 along which current is conducted also changes. As the size of the loop 15 changes, the point 16 at which the element 10 overlaps and contacts itself also changes.

An important aspect to the functionality of this embodiment is that the element 10 be resiliently deformable so as to maximise the size of the loop 15 and, thus, minimise the effective length of the element 10 between the connection points 12. In this regard, the arrangement and position of guide stitches 17 play an important role in the element 10 autonomously minimising the effective length of the element 10. Although not shown in the Figures, it is envisaged that the guide stitches 17 could at least partly, and possibly entirely be replaced by a guide structure that supports and guides the element 10 along a particular path. For example, the guide structure could be in the form of a tube, conduit or sleeve that partly or entirely encloses the element.

Figure 4:
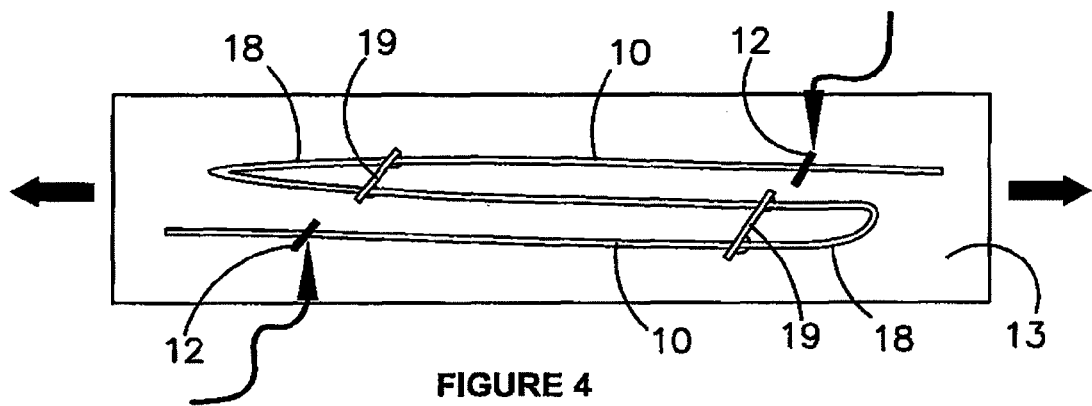

FIG. 4 illustrates a variation of the embodiment shown in FIG. 3 where two connection points 12 are fixed to the element 10 and anchored to the textile substrate 13. The element 10 is also configured so as to include two or more U-shaped sections 18 where the legs of the U-shape are interconnected by electrical conducting bridges 19 having low electrical resistance and effectively form a short circuit across each U-shape 18. The element 10 is able to slide through the bridges 19 such that the length of the element excluded from the effective length of the element can change.

In use, movement of the joint to which the embodiment is attached causes the connection points 12 to move away or toward each other and in the situation where the connection points 12 are moved away from each other, the element will slide through the bridges 19 reducing the size of the U-shapes and thereby increasing the effective length of the element 10.

Figure 5:
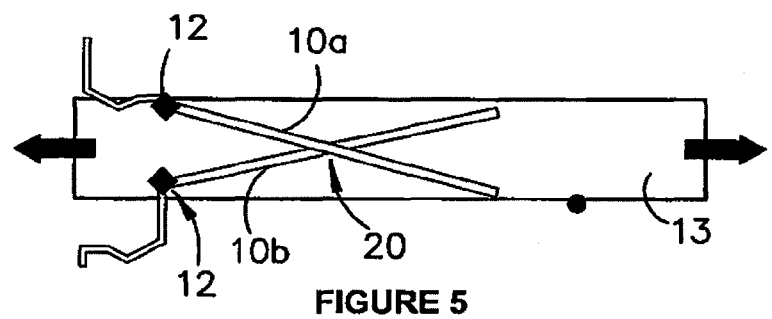
FIGS. 5 and 6 are schematic illustrations of yet another alternative motion detector suitable for mounting to a textile substrate according to a third embodiment of the present invention.

FIG. 5 illustrates an alternative embodiment in which the element 10 includes two separate sub-elements 10a and 10b held linearly in an X-shape that contact each other at a central point of interconnection 20. The point of interconnection 20 may or may not be located on a particular point on the substrate textile 13. The power connection points 12 are fixed to adjacent ends of each sub-element 10a and 10b and anchored to the textile substrate 13. The overall effective length of the element 10 is, therefore, a V-shape.

In use, movement of a joint to which the embodiment is attached causes the angle formed between the sub-elements 10a and 10b to change and, therefore, the point of interconnection 20 along the elements will also change. In the event that the point of interconnection 20 is located at a particular point on the textile 13, stretching the textile 13 in a direction shown by the arrows in FIG. 5 will cause the point of interconnection 20 to, in relative terms, move along the sub-elements 10a and 10b away from the power connection points 12. For example, in the situation where the point of interconnection and the power connection points 12 move away and, the length of the V-shape increases, the effective length of the element 10 defining the path of least electrical resistance also increases.

Figure 6:
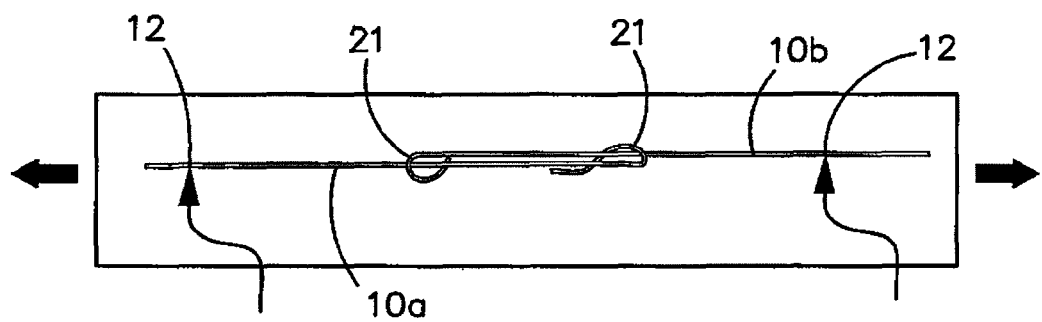

FIG. 6 illustrates a variation to the embodiment shown in FIG. 5 and includes two sub-elements 10a and 10b having substantially parallel axes. Opposite ends of the sub-elements 10a and 10b have a power source fixedly connected thereto and are mounted or anchored to the textile substrate 13. The other end of each sub-element 10a and 10b also includes a hook formation 21 that enables two adjacent sub-elements to engage each other such that in the section where the sub-elements 10a and 10b overlap the sub-elements 10a and 10b form parallel resistors.

In use, movement of a joint to which the embodiment is fitted will cause the power connection points 12 to move away or toward each other. In response to relative movement of the connection points 12, the hook formations 21 will allow each sub-element to slide over one another and change the extent to which the sub-elements 10a and 10b form parallel resistors. In other words, the effective length of the element 10 defining the path of the least resistance will change in response to movement between the connection points.

Each of the embodiments described above may include a flexible substrate, preferably a stretchable textile including an elastic material such as nylon, rubber, spandex or lycra™. The substrate may directly or indirectly be fitted to a machine or worn by a person that may or may not form part of garment. A typical example of the substrate would be that the substrate forms part of a knee or elbow brace.

Ideally, the elements or the sub-element mentioned above will be carbon loaded polyamide filaments or a silver coated nylon thread. These and any other types of electrical conducting elements that are robust and machine washable may be used as the element.

In addition, the element may be embedded within the textile and guided by an internal passageway or alternatively, as shown in FIGS. 1 to 6, located on top of the textile and directed in the desired direction by guide stitches.

Figure 7A:
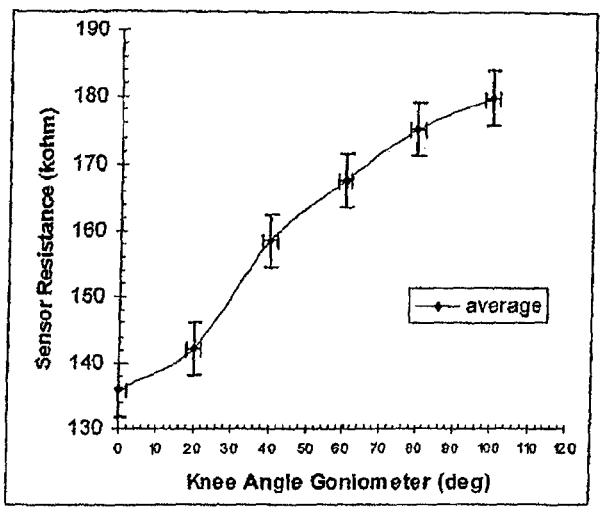
FIG. 7a is a graph of electrical resistance across an element as shown in FIG. 4 when fitted to a user's knee of as function of the flex of the knee.

FIGS. 7a through to 7c illustrate graphically the results of a trial carried out using a conventional elastic knee brace that had been modified to include a resiliently deformable element and two electrical power connection points that were generally configured according to the embodiment shown in FIG. 4.

Figure 7B:
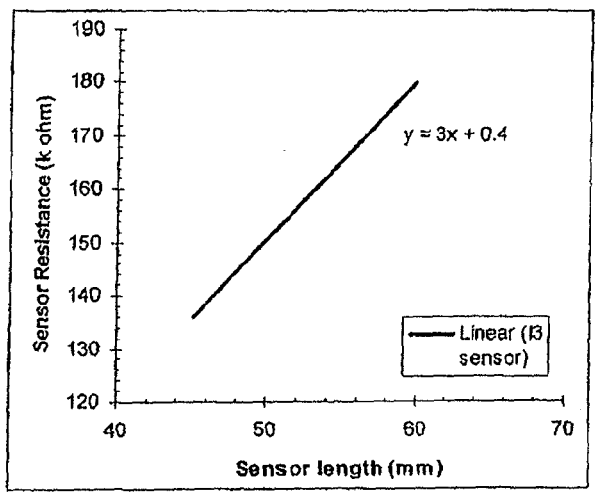
FIG. 7b is a graph of the electrical resistance of the element shown in FIG. 4 as a function of the effective length of the element.
Figure 7C:
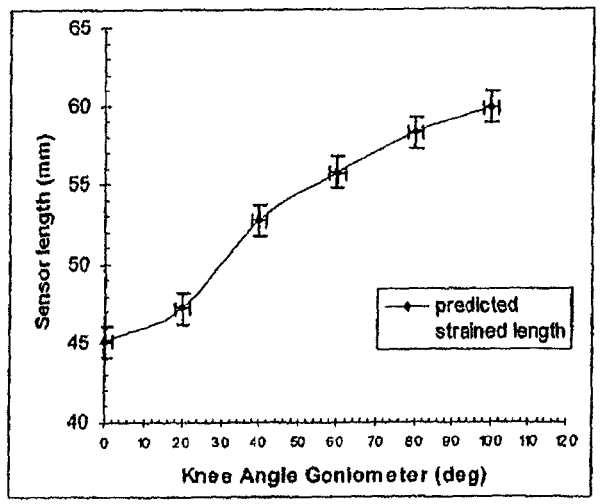
FIG. 7c is a graph of the effective length of the element as function of the flex of the user's knee similar to that shown in FIG. 7a using the element shown in FIG. 4.

FIG. 7a is a graph showing electrical resistance of the element is a function of the degree of flex of the knee. FIG. 7b is a graph showing that the resistance of the element is a linear function of the effective length of the element, and finally, FIG. 7c is a graph showing that the effective length of the element increases from approximately 45 mm when the knee is not flexed to approximately 60 mm when the knee is flexed to approximately 110 degrees.

The results provided in FIGS. 7a through to 7c can be used to calibrate the system so that it can be further used to record or analyse the knee flex of the person wearing the brace. Moreover, it will be appreciated that the effective length of the element between the connector points is also dependant on the design of the system and in particular the location of the connection points relative to each other and changes in shape and configuration of the element during movement. The electrical resistance of the effective length of the element is also dependant on the choice of resistive element and the conductive properties of the element. The resistive properties may be linear or non-linear. In any event in our experience it is preferred that the electrical resistance measured between the connection points have a resistance ranging from 10 to 300 k ohms, and suitable ranging from 10 to 100 k ohms.

Figure 8:
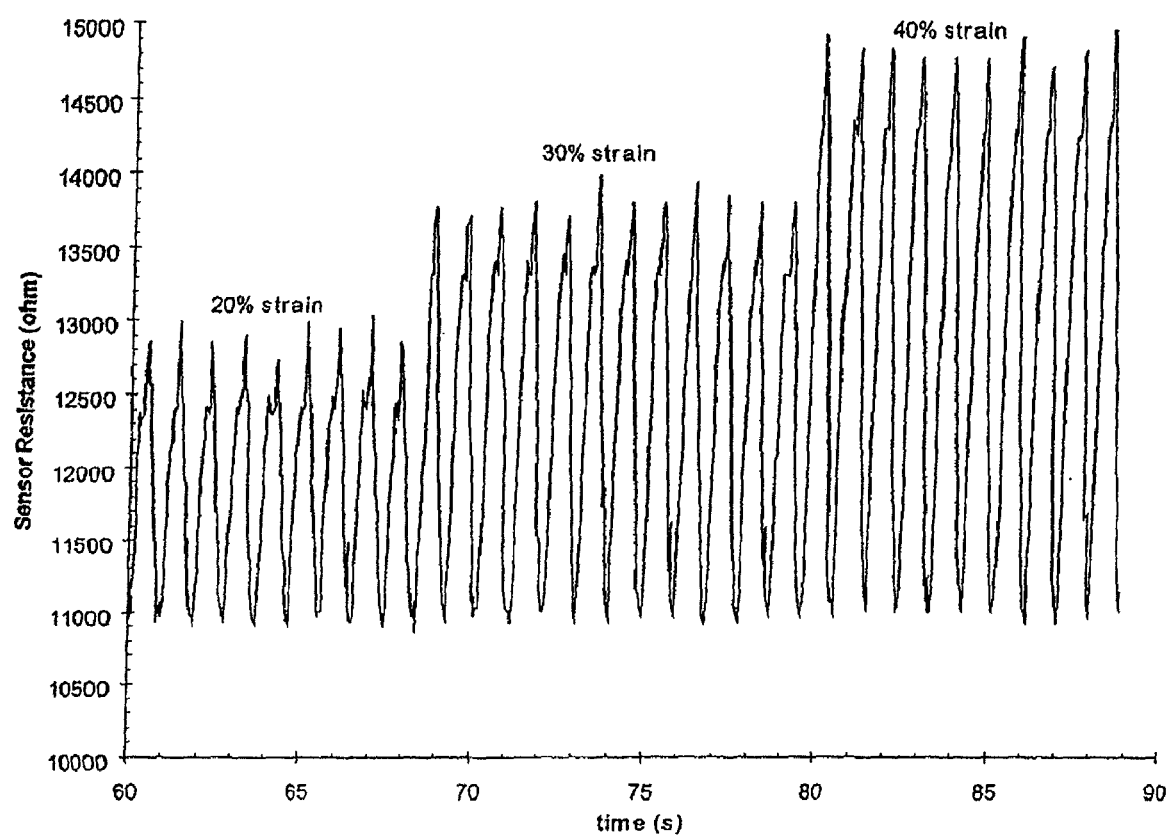
FIG. 8 is graph of electrical resistance of the element shown in FIG. 1 when elongated in the directions of the arrows in FIG. 1 at a frequency of the 1Hertz.

FIG. 8 graphically illustrates the electrical resistance of the element constructed as a loose knit structure fitted to a mechanical cyclic strain testing rig that is elongated in a cyclic fashion in a straightened positions at a frequency of 1 hertz (with very little flexing). The resiliently deformable element was generally configured according to the embodiment shown in FIG. 1. In this instance instead of the angle of flex being measured and used as basis for calibration, FIG. 8 illustrates the situation where the degree of elongation or stretch is measured in terms of the strain applied to the loosely knitted fabric sleeve.

In particular, the fabric is partially stretched such that the sensor is placed under a maximum strain of approximately 20%, 30% and 40%, for 10 second periods. The electrical resistance across the element is also measured. The result shown in FIG. 8 provide an alternative set of figures on which the system can be calibrated for flexural strain sensing.

A person skilled in the art of the present invention will appreciate that many modifications and variations may be made to the preferred embodiments and examples described without departing from the spirit and scope of the present invention.

For example, the preferred embodiments described the present invention in the context of a motion detector or a motion detecting system for detecting the movement of a person or an object. It will be appreciated that the movement detected or monitored by the present invention may be used for any purpose. For example, the movement may be analysed for training or rehabilitating skeletal joints or muscular injuries, biomedical monitoring, medical textiles, triage service for injured soldiers and other military and security applications. According to another example, the system may be applied to a medium such as the sail of the yacht, wherein the effective length of the element and, therefore the electrical resistance of the system is dependant on the shape and configuration of the sail. In other words, the trim and performance of the sail which is a function of the shape and configuration of the sail may ultimately be adjusted based on the electrical resistance measured by the system.

Changes in movement detected by the present invention may also be used to control an output such as sound from an electrical guitar. More particularly, the present invention may be configured for monitoring or detecting the movement of an elbow of the person and movement of the person's elbow reflects movement of the person's hands as if the person was placing their hands on the fret board or strumming the strings of a guitar.

In addition, the preferred embodiments mentioned above are examples in which the element is essentially a singular component member that is both conductive and resilient deformable in a direction transverse to its axis. Although not shown in the Figures, it is envisaged that the guide stitches 17 could at least partly, and possibly entirely replaced by a guide structure that supports and guides the element 10 along a particular path. The guide structure could be in the form of a tube or conduit that partly or entirely encloses the element and may be essentially non-elastic or elastic. In the situation where the guide structure is non-elastic, it is preferred that the guide structure be configured as a tube, conduit or sleeve through which the element slides with a minimum of friction. In the situation where the guide structure is elastic, it is preferred that the guide structure be configured as a tube, conduit or sleeve that is adapted to minimise the deformation of the element in a direction transverse to the longitudinal axis of the element such that the effective length of the element defines a path of least electrical resistance.

In the situation where the element is embedded within a textile or substrate, it is also possible that the guide structure be provided by passageway formed in the textile or substrate. The elastic properties of the textile either entirely, or in part, minimising the deformation of the element.

The claims defining the invention are as follows:

1. A system for detecting movement, the system comprising:
   a) at least two contactors configured to be mounted directly or indirectly to parts of a person or object that move relative to each other, such that when in use, the spacing between the contactors can change as a result of the person or object moving;
   b) an elongate electrical element electrically connected to the contactors such that, when in use, the electrical element conducts an electrical current, said electrical element being slidably connected to at least one of the contactors such that when the contactors are moved apart, the element slides in electrical connection with the one contactor; and
   c) a guide structure that guides the element along a particular path between the contactors, and
   wherein the element is substantially un-extendable along its longitudinal axis and resiliently deformable in a direction transverse to its longitudinal axis,
   wherein the resiliently deformable nature of the element minimizes deformation of the element in a direction transverse to its longitudinal axis and thereby minimizes the effective length of the element that defines a path of least electrical resistance between the contactors, and
   wherein relative movement of the contactors can cause the effective length of the element between the contactors to change such that movement can be measured or detected as a change in electrical resistance between the contactors.

2. The system according to claim 1, wherein the resilient deformable nature of the element minimizes the degree of curvature in the element between the contactors.

3. The system according to claim 1, further including an electrical power source in electrical connection with the element.

4. The system according to claim 1 further including a means for recording or monitoring the variations in electrical resistance between the contactors.

5. The system according to claim 4, wherein said means for recording the variations in electrical resistance includes a computer for analyzing the electrical resistance and analyzing movement of the object.

6. The system according to claim 1, further including a flexible substrate on which the contactors are mounted or attached.

7. The system according to claim 6, wherein when the substrate is fitted to a person or object, the substrate is configured to take up the shape of the person or object such that the contactors are held in substantially the same position on the object during movement.

8. The system according to claim 7 wherein the substrate is stretchable and the connectors are attached to the substrate so that when the substrate is stretched or folded the connectors move apart or away from each other.

9. The system according to claim 6, wherein the substrate is a textile and includes an elastic material including nylon, rubber, spandex, and lycra™.

10. The system according to claim 1 wherein element moves relative to the one contactor to which it is slidably connected under tension and when the contactors are moved toward each other the resilient deformable nature of the element enables the element to move relative to the contactor under compression.

11. The system according to claim 1, wherein the slidable connection between the element and the one contactor is in the form of the contactor partially or completely surrounding the element.

12. The system according to claim 1, wherein the element is slidably connected to both contactors.

13. The system according to claim 1, wherein the guide structure is a conduit, tube or sleeve in which the element can slidably move.

14. The system according to claim 13, wherein the guide structure is non-elastic.

15. The system according to claim 1, whereby when in use, the electrical resistance measured between the contactors ranges from 10 to 300 k ohms.

16. The system according to claim 1, whereby when in use, the electrical resistance measured between the contactors ranges from 10 to 100 k ohms.

* * * * *